United States Patent [19]

Schweighardt et al.

[11] Patent Number: 4,873,315

[45] Date of Patent: Oct. 10, 1989

[54] PERFLUORINATED PROPYL DERIVATIVE COMPOUNDS

[75] Inventors: Frank K. Schweighardt, Allentown; Webb I. Bailey, Fogelsville; John T. Lileck, Tamaqua; John K. Graybill, Macungie; Eugene G. Lutz, Drums, all of Pa.

[73] Assignee: Air Products and Chemicals, Inc., Allentown, Pa.

[21] Appl. No.: 89,293

[22] Filed: Aug. 25, 1987

[51] Int. Cl.$^4$ .................. C07C 19/08; C07C 17/02
[52] U.S. Cl. ................... 570/130; 228/42; 228/218; 514/832
[58] Field of Search .......................... 570/130

[56] References Cited

U.S. PATENT DOCUMENTS

| Re. 30,399 | 9/1980 | Ammann et al. | 228/180 |
|---|---|---|---|
| 2,459,782 | 1/1949 | McBee et al. | 570/130 |
| 2,487,820 | 11/1949 | McBee et al. | 260/648 |
| 2,631,170 | 3/1953 | Fowler | 260/648 |
| 3,775,489 | 11/1973 | Margrave et al. | 260/648 |
| 3,786,324 | 1/1974 | Kotschy | 317/258 |
| 4,106,557 | 8/1978 | Sonobe et al. | 165/105 |
| 4,143,079 | 3/1979 | Moore | 260/648 |
| 4,396,785 | 8/1983 | Kobayashi et al. | 570/129 |
| 4,453,028 | 6/1984 | Lagow | 570/130 |
| 4,549,686 | 10/1985 | Sargent et al. | 570/130 |
| 4,739,112 | 4/1988 | Savu | 570/130 |

FOREIGN PATENT DOCUMENTS

| 0194009 | 9/1986 | European Pat. Off. |
|---|---|---|
| 785641 | 10/1957 | United Kingdom . |
| 1281822 | 7/1972 | United Kingdom . |
| 2110204 | 6/1983 | United Kingdom . |

OTHER PUBLICATIONS

Organic Fluorides Part V Fluorination of Hydrocarbons with Cobalt Trifluoride, R. N. Hasqeldine and R. Smith, Journal of Chemistry Society (1950).

"Ternary Systems of Liquid Sulfur Dioxide"—Alfred W. Francis, Journal of Chemical and Engineering Data, vol. 10, No. 1 (Jan. 1965).

"Ternary Systems of Sulfur and Sulfur Compounds'—Alfred W. Francis, Journal of Chemical and Engineering Data, vol. 11, No. 4 (Oct. 1966).

*Primary Examiner*—J. E. Evans
*Attorney, Agent, or Firm*—Geoffrey L. Chase; James C. Simmons; William F. Marsh

[57] ABSTRACT

Novel compositions include compounds of the formula:

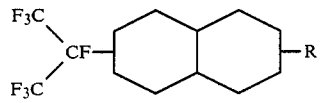

wherein the carbon rings are fully fluorinated and R is selected from the group consisting of fluorine, —$CF_3$ or —$CF(CF_3)_2$.

2 Claims, No Drawings

PERFLUORINATED PROPYL DERIVATIVE COMPOUNDS

TECHNICAL FIELD

The present invention is related to the field of perfluorinated, alkyl-substituted, condensed ring compounds. More specifically, the present invention is directed to various propyl and methyl derivatives of decahydronaphthalene prepared from naphthalene, which former compound is then fully fluorinated.

BACKGROUND OF THE PRIOR ART

Fluorinated carbon compounds are finding increasing utility in modern industry, such as the electronics fabrication industry, and researchers have found heightened interest in fluorinated compounds for various biological and medical applications, such as synthetic blood and diagnostic fluids.

Perfluorinated multiple condensed ring compounds have been known for a significant period of time, such as perfluorophenanthrene as disclosed in U.S. Pat. No. 2,487,820. That patent makes a broad, general and unsupported disclosure that:

"Fused-ring aromatic hydrocarbons such as anthracene, naphthalene, phenanthrene and their substitution derivatives, can be fluorinated readily with the addition of fluorine atoms at the points of unsaturation and, if desired, with the replacement of hydrogen in the molecule, and the production of saturated fluorine-containing compounds."

Partially fluorinated compounds are exemplified by the 1-methyl(3,3,3-trifluoropropyl) naphthalene compounds disclosed in U.S. Pat. No. 4,396,785. These compounds are only marginally fluorinated and the condensed carbon rings retain their unsaturated aromatic character.

The tertiary butyl derivatives of a single carbon ring, cyclohexene, is disclosed in U.S. Pat. No. 4,453,028.

Perfluoro-2-methyldecahydronaphthalene has been reported to have been synthesized from 2-methyl naphthalene using cobalt trifluoride fluorination technology as set forth in an article titled *Organic Fluorides. Part V. Fluorination of Hydrocarbons With Cobalt Trifluoride*, by R. N. Haszeldine and F. Smith appearing in Journal of Chemistry Society (1950) pages 3617 to 3623.

The cobalt trifluoride fluorination of 1-methyl decahydronaphthalene to produce perfluoro-1-methyl decahydronaphthalene has also been set forth in British Pat. No. 1,281,822. Fluorination of substituted naphthalenes is generally disclosed.

The basic technique for cobalt trifluoride fluorination is set forth in U.S. Pat. No. 2,631,170.

U.S. Pat. No. 3,775,489 is directed to the fluorination of various aromatic carbon compounds of the naphthalene and anthracene class.

U.S. Pat. No. 3,786,324 discloses a utility for perfluorinated hydrocarbons comprising dielectric fluids for capacitors. The compound 1-trifluoromethylperfluorodecahydronaphthalene is mentioned as a potential dielectric fluid.

U.S. Pat. No. 4,106,557 describes a refrigeration apparatus utilizing various halogenated carbon refrigerants, including cyclic fluorinated carbon ethers.

U.S. Pat. No. 4,143,079 discloses a perfluorinated 1-methyl-4-isopropyl cyclohexane. This material is recited to have utility as an artificial blood component.

U.S. Pat. No. Re. 30,399 discloses a technique for soldering electronic components in a mass production mode in the heated vapor of a boiling fluid wherein the vapor condenses on cold solder to be reflowed and the solder is melted by the heat of vaporization evolved during the condensation of the adhering fluid vapor. This form of soldering is known as vapor phase soldering, condensation soldering and various reflow soldering nomenclatures. The criteria delineated for a heat transfer liquid for such soldering includes: a boiling point above the melting point of the solder wherein the boiling point is preferably sharply defined and dependent upon a single component rather than multicomponent materials, electrically non-conducting characteristics, vapors which are non-oxidizing, chemically stable and inert, non-toxic, non-inflammable and relatively denser than air, relatively high latent heat of vaporization, and degreasing properties. Fluorinated polyoxypropylene is a disclosed fluorocarbon suitable for heat transfer liquid choice.

U.S. Pat. No. 4,549,686 describes vapor phase soldering using perfluorotetradecahydrophenanthrene (perfluorophenanthrene).

British Pat. No. 785,641 discloses the fluorination of various carbon compounds with hydrogen fluoride wherein such compounds include benzene, toluene, anthracene and diamylnaphthalene. Retene, which is 1-methyl-7-isopropyl phenanthrene, is also capable of the recited fluorination treatment.

U.K. patent application No. 2110204A discloses various perfluoroalkyl-cyclohexane mixtures useful for vapor phases soldering in the boiling range of 180° to 300° C. These materials are produced by the fluorination of narrow cut linear alkylbenzene compounds with cobalt trifluoride.

European patent application No. 0 194 009 discloses fluorochemical compositions comprising compounds in the form of perfluoropolycycloalkane ring assemblies having (a) at least two perfluorinated cyclohexane rings, (b) at least two perfluorinated fused ring systems, or (c) a combination of at least one perfluorinated fused ring system with at least one perfluorinated cyclohexane ring, each perfluorinated ring or ring system being directly joined to another perfluorinated ring or fused ring system by a single bond. The rings may have certain substituent groups.

The prior art fluorination compounds have failed to provide a stable, inert perfluoro compound having a desirable sharp boiling point in the approximate range of 215° C. which is most desirable for presently existing vapor phase soldering utilities. In addition, the prior art compounds suffer from various levels of susceptibility to heat degradation to hydrogen fluoride and perfluoroisobutylene, as well as having undesirable fluorine utilizations due to significant levels of aliphatic character. The present invention overcomes these shortcomings.

BRIEF SUMMARY OF THE INVENTION

The present invention is a perfluorinated compound of the formula:

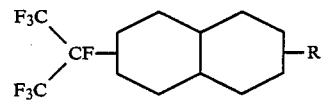

wherein the carbon rings are fully fluorinated and R is selected from the group consisting of fluorine, —CF₃ or —CF(CF₃)₂.

One of the preferred species of the compounds of the present invention is the perfluorodiisopropyl substituted decahydronaphthalene compound. Another preferred compound is the perfluorodiisopropyl substituted decahydronaphthalene wherein the substitution is in the 2 and 7 positions. Yet another of the preferred compounds of the present invention is the perfluoromethylisopropyl substituted decahydronaphthalene compound. Preferably, the perfluoromethyl radical is in the number 2 position on the decahydronaphthalene ring. Alternately, the perfluoromethyl substituent is in the number 1 position on the decahydronaphthalene ring. Finally, one of the preferred species of the present invention is the perfluorinated monoisopropyl substituted decahydronaphthalene compound, particularly where the perfluorinated monoisopropyl substituent is in the number 2 position.

The present invention is also directed to a method for utilizing such compounds wherein it comprises a method of soldering a component to be soldered by immersing a component in the vapor bath to melt the solder, and the component is then withdrawn from the vapor bath, the improvement comprising that the vapor bath is composed substantially of compounds having the formula:

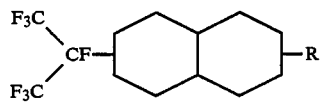

wherein the carbon rings are fully fluorinated and R is selected from the group consisting of fluorine, —CF₃ or —CF(CF₃)₂. The vapor bath can comprise mixtures of the recited compounds with other compounds such as perfluorophenanthrene.

DETAILED DESCRIPTION OF THE INVENTION

The various perfluorinated isopropyl derivatives of decalin, which constitute the subject matter of the present invention, are valuable as inert constant boiling fluids required by the electronic fabrication industry for the manufacture and testing of various electronic components. Fluids boiling in the temperature range of 150°–250° C. are of interest to the electronics industry for these applications. Currently, various suppliers of fluorinated fluids provide a series of compounds that meet the 150°–250° C. temperature range which are based on, for example, perfluorinated tertiary amines. There is some question on the stability of these materials at elevated temperatures. One concern arises from incomplete fluorination, which results in residual hydrogen. These partially fluorinated compounds have been shown to undergo decomposition at elevated temperatures resulting in the formation of HF and perfluoroisobutylene.

Another class of compounds that are currently supplied to meet the needs for a 150°–250° C. boiling fluid are based on perfluoropolyethers. These polyethers are prepared by the oxidative polymerization of tetrafluoroethylene. To obtain the various boiling ranges, the polyethers are distilled into different fractions. The final product does not constitute a single compound, but rather a mixture of molecular weight ranges. This results in a product, that with time will increase in boiling temperature as the lower molecular weight fractions are removed by differential boil-off.

The compositions of the present invention constitute essentially single compounds having sharply defined boiling points which do not fractionate off into various components through exposure to cycling from cool-down to high temperature utilization, such utilization as is characteristic of vapor phase soldering fluid utility. For the sake of clarity the numbering of the carbons on the decahydronaphthalene ring (fully saturated naphthalene derivative) are set forth below.

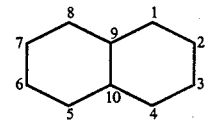

The perfluoroisopropyldecahydronaphthalene compound of the present invention, which is preferably substituted at the number 2 position of the decahydronaphthalene ring, has an empirical formula of $C_{13}F_{24}$ and a molecular weight of 612. The material is a liquid at room temperature with a boiling point of approximately 200° C. The general structure of the compound of the present invention has been confirmed by ¹⁹F NMR (nuclear magnetic resonance spectroscopy) and GC/MS (gas chromatography/mass spectroscopy). Typically, the feedstock to produce such a perfluorinated compound is the hydrocarbon diisopropylnaphthalene, which can be prepared by the alkylation of naphthalene by known techniques. The new composition of the present invention is substantially a perfluorinated analog of the above hydrocarbon starting material wherein all aromatic character, hydrogen and one isopropyl group are removed as a result of the reaction process. All isomers and conformers of monoisopropylnaphthalene are represented by the perfluorinated compound of the present invention.

The perfluorodiisopropyldecahydronaphthalene compound of the present invention, which is preferably substituted at the number 2 and number 7 positions of the decahydronaphthalene ring, has an empirical formula of $C_{16}F_{30}$ and a molecular weight of 762. This material is liquid at room temperature with a boiling point of approximately 240° C. The general structure has been confirmed by ¹⁹F NMR and GC/MS.

The feedstock for the production of this species of the compounds of the present invention is the hydrocarbon diisopropylnaphthalene which can be again prepared by the alkylation of naphthalene by known techniques. The composition is substantially a perfluorinated analog of the hydrocarbon starting material with all aromatic character and hydrogen removed, but the isopropyl substituents remaining intact. All isomers and conformers of diisopropylnaphthalene are represented by this invention.

The perfluoroisopropyl-1-methyldecahydronaphthalene and perfluoroisopropyl-2-methyldecahydronaphthalene species of the isopropyl, methyl-substituted decahydronaphthalene compounds of the present invention have an empirical formula of $C_{14}F_{26}$ and a molecular weight of 662. The materials are liquid at room temperature with boiling points of approximately 219° C. Again, these structures have been confirmed by ¹⁹F NMR and GC/MS. The feedstocks are hydrocarbon isopropylmethyl derivatives of naphthalene such as isopropyl-1-methylnaphthalene and isopropyl-2-methylnaphthalene which are prepared by known alkylation techniques of naphthalene. The compositions of matter described immediately above are substantially perfluorinated analogs of the hydrocarbon starting materials with all aromatic character and hydrogen removed. All isomers and conformers of isopropylmethylnaphthalene are represented by this invention. Although the number 1 position and the number 2 position methyl derivatives are preferred examples of the present invention, it is appreciated that other position isomers are included within the scope of this contemplated composition class.

All of these species of the compounds of the present invention have utility for oxygen transport media for in vivo and in vitro use as pure substances or mixtures or emulsions, as well as use as hydraulic fluids, lubricants, heat exchange or cooling fluids and other such applications where chemical inertness and boiling point are the desired physical and chemical properties, most particularly vapor phase soldering. Various of the compounds have been tested as vapor phase soldering fluids. The fluids were heated at reflux for an extended period of time and showed no evidence of decomposition, wherein a printed circuit board which contained a solder silk screen and a surface mounted device was immersed into the reflux vapor area and the solder reflow occurred within 30 seconds. This demonstrated successful and acceptable vapor phase soldering utility.

At this time, the preparation and identification of the compounds of the present invention will be set forth in the following examples and tables.

EXAMPLE 1

(Notebook 7820-7297-17,18)

Twenty grams of di-isopropyl naphthalene was vaporized and charged to a reactor containing sufficient cobalt trifluoride to carry out the reaction. The temperature of the cobalt trifluoride bed was set at approximately 630°–650° F. Gaseous products from the reaction were collected in traps held at 0° C. and −70° C. In run 17, 26.4 gms of crude fluorochemical and 26.3 gms of HF were collected. In run 18, performed under essentially identical conditions, 30.9 gms of crude fluorochemical and 37 gms of HF were produced.

EXAMPLE 2

(Notebook 7820-6832-92,94)

Crude fluorochemical of run 7297-17 was neutralized with 2M KOH and phase separated to give 21.3 gms of fluorinated material. By the same procedure, run 7297-18 resulted in 28.35 gms of fluorochemical product. Specific gravities of 2.04 gm/ml and 2.02 gm/ml respectively were found indicating a perfluorinated product.

The neutralized material obtained above was combined and a total of 27.38 gms of the fluorochemical was distilled. A pot reflux temperature of 186° C. was shown with clear liquids distilled at pot temperatures ranging from 203° C to 265° C. Yield of compound (1) [pot temperature 203°–214° C.] was found to be 30.7% (perfluoromonoisopropyldecahydronaphthalene) and compound (2) [pot temp. 221°–265° C.], 40.2% (perfluorodiisopropyldecahydronaphthalene).

EXAMPLE 3

(Notebook 7820-7297-21)

A total of 62.3 gms of crude fluorochemical produced via the cobalt trifluoride fluorination of di-isopropyl naphthalene in previous runs was passed through the fluorination reactor at harsher conditions. Reactor temperatures of 800° F. were employed and a total of 41.7 gms of product fluorochemical was collected.

EXAMPLE 4

(Notebook 7820-6832-97)

Crude fluorochemical obtained from run 7297-21-19 was distilled. A total of 39.39 gms was charged to the distillation apparatus and found to have a pot reflux temperature of 149° C. Subsequent distillation was done resulting in a clear liquid with a specific gravity of 1.96–2.01 gm/ml distilling at a pot temperature range of 149°–214° C. and comprising 75.3% of the material charged. This material is comprised substantially of compound (1), namely perfluoromonoisopropyldecahydronaphthalene, resultant from the removal of a single isopropyl group from the parent molecule at the harsher fluorination conditions.

EXAMPLE 5

(Notebook 7820-8832-90,91)

A total of 1884 grams of di-isopropyl naphthalene was fed to a pilot scale reactor (12" diameter × 10' long) filled with sufficient cobalt trifluoride powder (~375 lbs) to affect complete fluorination. The organic was introduced into the reactor by vaporization from a heated pot (450° F. start–525° F. finish) purged with $N_2$ gas (1500 sccm). Reactor temperatures were held at 660° F. and the cobalt trifluoride bed was continuously stirred in the reaction zone by an agitator running at 2–3 rpm. Gases from the reactor were continually fed to a dust removal trap and heat exchanger (30° F.) where crude fluorochemical product was condensed.

EXAMPLE 6

(Notebook 7820-8220-66,67,68)

Crude fluorochemical product from the above and similar runs were combined and further purified to remove HF and partially fluorinated by-products. A total of 6000 grams of the purified material was then charged to a distillation apparatus and distilled. A total of 1558 grams (26% of the charge) was found to be distilled at a head temperature of 190°–205° C. This material was later identified by $19^F$ NMR and GC/MS to be substantially compound (1) namely, perfluoromonoisopropyldecahydronaphthalene. A further portion, 1267 grams (21.1% of the charge) was found to distill at a head temperature of 240°–245° C. This material was later identified by $19^F$ NMR and GC/MS to be substantially compound (2) namely, isopropyldecahydronaphthalene.

TABLE 1

Analytical Characterization of Perfluoromonosisopropyldecahydronaphthalene

| $^a$NMR - $^{19}$F | $CF_3$ −68 to −74 multiplet | $CF_2$ −90 to −150 multiplet | CF −170 to −190 multiplet |
|---|---|---|---|
| Relative F Atomic Ratio calculated | 1.5 | 3.5 | 1.0 |

TABLE 1-continued
Analytical Characterization of Perfluoromonosisopropyldecahydronaphthalene

| $^a$NMR - $^{19}$F | $CF_3$<br>−68 to −74<br>multiplet | $CF_2$<br>−90 to −150<br>multiplet | $CF$<br>−170 to −190<br>multiplet |
|---|---|---|---|
| observed | 1.4 | 3.9 | 1.0 |
| $^b$MASS SPECTRUM (m/e) | | | |
| calculated | | 612 ($C_{13}F_{24}$) | |
| observed | | 612 ($C_{13}F_{24}$) | |

$^a$in $CDCl_3/C_2Cl_3F_3$
$^b$electron ionization and/or chemical ionization with $CH_4$

TABLE 2
Analytical Characterization of Perfluorodiisopropyldecahydronaphthalene

| $^a$NMR - $^{19}$F | $CF_3$<br>−68 to −74<br>multiplet | $CF_2$<br>−90 to −150<br>multiplet | $CF$<br>−170 to −190<br>multiplet |
|---|---|---|---|
| Relative F Atomic Ratio | | | |
| calculated | 2.0 | 2.0 | 1.0 |
| observed | 2.1 | 2.3 | 1.0 |
| $^b$MASS SPECTRUM (m/e) | | | |
| calculated | | 762 ($C_{16}F_{30}$) | |
| observed | | 762 ($C_{16}F_{30}$) | |

$^a$in $CDCl_3/C_2Cl_3F_3$
$^b$electron ionization and/or chemical ionizaton with $CH_4$

EXAMPLE 7
(Notebook 7826-8876-80)

25.00 g of isopropyl-1-methylnaphthalene were charged to a sample cylinder and connected to an enclosed hotplate operating at 290° C. The isopropyl-1-methyl naphthalene was fed into the hotplate by a metering pump at a rate of 10.3 g/hr into a 15.5 sccm nitrogen stream. The organic/nitrogen stream was carried into a cobalt trifluoride reactor 10 cm in diameter and 60 cm long containing approximately 3000 g cobalt trifluoride. The reactor was heated with a three zone furnace operating at 285°, 285° and 315° C., respectively. The isopropyl-1-methyl naphthalene feed was subsequently converted to a perfluorochemical in the reactor and was collected in a trap held at 25° C. 67.7 g of a light yellow liquid was collected. Additional material was produced under similar reactor conditions.

EXAMPLE 8
(Notebook 7826-8490-51)

92.5 g of the combined cobalt trifluoride products were charged to a 40 ml stainless steel sample cylinder for a direct fluorination clean-up step. A fluorine/nitrogen gas mixture increasing to 100% fluorine with time was sparged into the liquid at 25° C. and 150° C. Approximately 1.0 g of elemental fluorine was added into the crude perfluorochemical mixture.

EXAMPLE 9
(Notebook 7826-8490-52)

59.4 g of the directly fluorinated product from above was distilled in a micro spinning band still. A fraction boiling at 219° C. was collected which represented 43.3% (by GC) of the original charge. The fluorochemical was identified as perfluoro, isopropyl-1-methyl-decahydronaphthalene. Analytical information is shown in Table 3.

EXAMPLE 10
(Notebook 7826-9497-5)

25.00 g of isopropyl-2-methylnaphthalene were charged to a sample cylinder and connected to an enclosed hotplate operating at 300° C. The isopropyl-2-methylnaphthalene was fed onto the hotplate by a metering pump at a rate of 9.7 g/hr into a 15.5 sccm nitrogen stream. The organic/nitrogen stream was carried into a cobalt trifluoride reactor 10 cm in diameter and 60 cm long containing approximately 3000 g cobalt trifluoride. The reactor was heated with a furnace operating at 300° C. The isopropyl-2-methylnaphthalene feed was subsequently converted to 52.0 g of perfluoro, isopropyl-2-methyldecahydronaphthalene as identified by GC/MS [calculated m/e 662 ($C_{14}F_{26}$); observed m/e 662 ($C_{14}F_{26}$)].

TABLE 3
Analytical Characterization of Perfluoro, isopropyl-1-methydecahydronaphthalene

| $^a$NMR - $^{19}$F | $CF_3$<br>−64 to −75$^b$<br>multiplet | $CF_2$<br>−100 to −145$^b$<br>multiplet | $CF$<br>−165 to −190$^b$<br>multiplet |
|---|---|---|---|
| Relative F Atomic Ratio | | | |
| calculated | 1.8 | 2.4 | 1.0 |
| observed | 1.6 | 2.6 | 1.0 |
| $^c$MASS SPECTRUM (m/e) | | | |
| calculated | | 662 ($C_{14}F_{26}$) | |
| observed | | 643 ($C_{14}F_{26}$—F) | |

$^a$in $CDCl_3/CCl_3F$
$^b$ppm from $CCl_3F$
$^c$electron ionization and/or chemical ionzation with $CH_4$

EXAMPLE 11
(Notebook 7826-8490-102)

A glass vapor phase soldering apparatus consisting of a 100 ml flask connected to a condenser was used to demonstrate vapor phase soldering with perfluoro, isopropyl methyl decahydronaphthalene. A solder paste consisting of 96.5% tin and 3.5% silver was used to coat a printed circuit board. A surface mount device was positioned on the solder paste and the entire assembly was immersed in perfluoro, isopropyl methyl decahydronaphthalene which had been heated to reflux temperature. Solder reflow was observed to occur in approximately 26 seconds. Upon removal of the circuit assemble, no fluorochemical residue was observed, but clean substantial reflow of the solder was observed and the assembly comprising the surface mounted device and printed circuit board were firmly affixed by the operation of the solder.

These compounds of the present invention have particularly desirable utility in a method of soldering a component to be soldered by immersing a component in the vapor bath to melt the solder, and the component is then withdrawn from the vapor bath, the improvement comprising that the vapor bath is composed substantially of compounds having the formula:

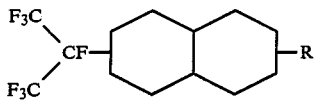

wherein the carbon rings are fully fluorinated and R is selected from the group consisting of fluorine, —CF$_3$ or —CF(CF$_3$)$_2$. The compounds can be mixed with one another or other compounds such as perfluorophenanthrene. Vapor phase soldering is described in U.S. Pat. No. 30,399 and U.S. Pat. No. 4,549,686, both of which are incorporated herein by reference.

The compounds of the present invention succeed in overcoming the drawbacks of various of the compounds of the prior art, particularly for utility in vapor phase soldering fluid use. The compounds of the present invention exhibit all of the desired attributes of a vapor phase soldering fluid as identified in U.S. Pat. No. Re. 30,399 described above. Included in these attributes which the compounds in the present invention exhibit are: low toxicity, chemical inertness, lack of flammability, appropriate dielectric characteristics, degreasing properties, sharply defined boiling point, a vapor denser than air and relatively high latent heat of vaporization. Specifically, these compounds have low potential for evolution of HF and perfluoroisobutylene when subjected to long term cyclic heating and cooling typical of vapor phase soldering use.

The present invention has been set forth with regard to various spcific examples and embodiments of the invention. However, the scope of the invention should be ascertained from the claims which follow.

We claim:

1. The perfluorinated compounds having the formula:

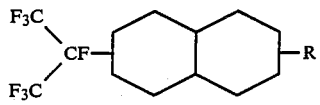

wherein the carbon rings are fully fluorinated.

2. The perfluorinated compound of claim 1 having the formula:

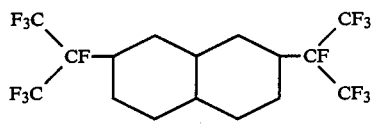

wherein the carbon rings are fully fluorinated.

* * * * *

UNITED STATES PATENT AND TRADEMARK OFFICE
CERTIFICATE OF CORRECTION

PATENT NO. : 4,873,315

DATED : October 10, 1989

INVENTOR(S) : Schweighardt, et al

It is certified that error appears in the above-identified patent and that said Letters Patent is hereby corrected as shown below:

Cover page (75) Inventors: delete "Frank K. Schweighardt, Allentown; Webb I. Bailey, Fogelsville:"

Column 10, formula under Claim 1 should be:

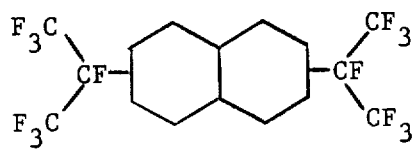

Signed and Sealed this

Ninth Day of October, 1990

Attest:

HARRY F. MANBECK, JR.

Attesting Officer     Commissioner of Patents and Trademarks